United States Patent [19]

Teles et al.

[11] Patent Number: 5,359,094
[45] Date of Patent: Oct. 25, 1994

[54] PREPARATION OF GLYCERYL CARBONATE

[75] Inventors: Joaquim H. Teles, Ludwigshafen; Norbert Rieber, Mannheim; Wolfgang Harder, Weinheim, all of Fed. Rep. of Germany

[73] Assignee: BASF Aktiengesellschaft, Ludwigshafen, Fed. Rep. of Germany

[21] Appl. No.: 99,142

[22] Filed: Jul. 29, 1993

[30] Foreign Application Priority Data

Aug. 5, 1992 [DE] Fed. Rep. of Germany ....... 4225870

[51] Int. Cl.$^5$ ............................................. C07D 317/36
[52] U.S. Cl. .................... 549/228; 549/229; 549/230
[58] Field of Search ..................... 549/228, 229, 230

[56] References Cited

U.S. PATENT DOCUMENTS

| | | | |
|---|---|---|---|
| 2,856,413 | 10/1958 | Malkemas et al. | 549/228 |
| 3,153,051 | 10/1964 | Kormendy et al. | 549/229 |
| 3,379,693 | 4/1968 | Hostettler et al. | 549/229 |
| 4,231,937 | 11/1980 | Kao et al. | 549/229 |
| 4,314,945 | 2/1982 | McMullen et al. | 549/229 |
| 4,344,881 | 8/1982 | Strege et al. | 549/229 |
| 4,483,994 | 11/1984 | Jacobson | 549/229 |
| 4,658,041 | 4/1987 | Renga | 549/229 |
| 4,835,289 | 5/1989 | Brindöpke | 549/229 |
| 5,091,543 | 2/1992 | Grey | 549/229 |
| 5,118,818 | 6/1992 | Delledonne et al. | 549/229 |

FOREIGN PATENT DOCUMENTS

| | | |
|---|---|---|
| 2222488 | 11/1972 | Fed. Rep. of Germany . |
| 2265228 | 12/1976 | Fed. Rep. of Germany . |
| 1382313 | 1/1975 | United Kingdom . |

*Primary Examiner*—Cecilia Tsang
*Attorney, Agent, or Firm*—Keil & Weinkauf

[57] ABSTRACT

A process for the preparation of glyceryl carbonate by causing glycerol to react with carbon monoxide and oxygen in the presence of a Group Ib, Group IIb, or Group VIIIb catalyst as per the Periodic Table at temperatures ranging from 0° to 180° C.

4 Claims, No Drawings

PREPARATION OF GLYCERYL CARBONATE

The present invention relates to a process for the preparation of glyceryl carbonate by the reaction of glycerol with carbon monoxide and oxygen in the presence of Group Ib, Group IIb, and Group VIIIb catalysts as per the Periodic Table and the conversion thereof to glycidol at elevated temperatures over alkali metal salts and/or alkaline earth metal salts.

DE-A 2,222,488 and DE-A 2,265,228 describe processes for the preparation of ethylene carbonates from glycols using $CO/O_2$ in the presence of Group Ib, Group IIb, and Group VIIIb catalysts.

U.S. Pat. No. 2,856,413 describes the dissociation of glyceryl carbonate to produce glycidol over phosphates, pyrophosphates, chlorides, bromides, acetates, bicarbonates, and carbonates of alkali metals and alkaline earth metals.

It is thus an object of the present invention to provide a process which makes it possible to prepare glyceryl carbonate starting from glycerol and to find means for the conversion thereof to glycidol.

Accordingly, we have found a novel and improved process for the preparation of glyceryl carbonate, wherein glycerol is caused to react with carbon monoxide and oxygen in the presence of a Group Ib, IIb, or VIIIb catalyst as per the Periodic Table at temperatures ranging from 0° to 150° C. and the conversion thereof to glycidol by reaction at temperatures ranging from 80° to 300° C. and pressures of from 0.001 to 5 bar over alkali metal salts and/or alkaline earth metal salts.

The process of the invention may be carried out as follows:

The reaction can be started by feeding a gaseous mixture of carbon monoxide and oxygen into the reaction mixture. The composition of the gas mixture can be varied as desired within wide limits. Air can be used instead of oxygen if desired, for example, or the gas mixture can be diluted, if desired, with an inert gas such as nitrogen, argon or carbon dioxide. Generally speaking, a $CO:O_2$ molar ratio of from 100:1 to 0.5:1 and preferably from 50:1 to 1:1 and more preferably from 20:1 to 1.5:1 is used.

The reaction gases carbon monoxide and oxygen are introduced into the liquid present in the reactor. To ensure better intermixing and dispersion of the reaction gases in the reactor, it is preferred to use additional mechanical stirring means. Suitable types of reactor are stirred boilers or stirred autoclaves or bubble reactors which are advantageously capable of being heated and which may also be equipped with stirring means, if desired.

The reaction can be advantageously carried out under elevated pressure, generally under a pressure of from 1 to 100 bar and preferably from 2 to 10 bar and more preferably from 2.5 to 5 bar, optionally in the presence of an inert solvent. The reaction temperature generally ranges from 0° to 180° C. and preferably from 80° to 150° C. and more preferably from 100° to 140° C.

The reaction may be carried out continuously or batchwise. In the preferred continuous mode of operation, the reaction gases are usually used in excess and the unconverted gas is circulated.

Suitable catalysts are those containing elements in Groups Ib, IIb, and VIIIb in the Periodic Table such as salts of the elements copper, silver, gold, zinc, cadmium, mercury, iron, cobalt, nickel, ruthenium, rhodium, palladium, osmium, iridium and/or platinum and preferably salts of the elements copper, silver, mercury, iron, cobalt and/or nickel and more preferably salts of the elements copper and/or mercury.

Suitable salts are sulfates, chlorides, bromides and trifluoroacetates and preferably chlorides, bromides and trifluoroacetates. Suitable copper catalysts for use in the process of the invention are generally simple copper salts such as copper halides, copper(I) sulfate, copper (alkoxy)halides and copper(I) trifluoroacetate and preferably copper(I) halides such as copper(I) chloride and copper(I) bromide and copper(I) sulfate and copper(I) trifluoroacetate.

Suitable inert solvents are tertiary amines such as $C_3$–$C_{20}$tertiary amines, e.g., trimethylamine, pyridine, quinoline, α-, β-, and γ-picolines and preferably pyridine and γ-picoline, nitriles such as acetonitrile, propionitrile and benzonitrile, nitro compounds such as nitrobenzene and preferably benzonitrile or esters such as $C_2$–$C_{20}$alkyl carboxylates, e.g., methyl acetate, ethyl acetate, ethyl benzoate and preferably ethyl benzoate and lactones such as butyrolactone, ureas such as tetramethyl urea and carbonates such as propylene carbonate.

The conversion of the glyceryl carbonate to glycidol can be carried out at temperatures ranging from 100° to 300° C. and preferably from 125° to 275° C. and more preferably from 210° to 250° C. and pressures of from 0.001 to 5 bar and preferably from 0.005 to 2 bar and more preferably from 0.01 to 1 bar over alkali metal salts and/or alkaline earth metal salts, for example, in distillation apparatus.

Suitable salts of alkali metals and alkaline earth metals are halides such as fluorides, chlorides, bromides, and iodides, phosphates, monohydrogenphosphates, dihydrogen phosphates, pyrophosphates, sulfates, borates, acetates, carbonates and bicarbonates and preferably fluorides, iodides, and sulfates and more preferably fluorides, sulfates and borates. Specific examples thereof are:

lithium fluoride, sodium fluoride, potassium fluoride, rubidium fluoride, cesium fluoride, berylium fluoride, magnesium fluoride, calcium fluoride, strontium fluoride, barium fluoride, lithium chloride, sodium chloride, potassium chloride, rubidium chloride, cesium chloride, berylium chloride, magnesium chloride, calcium chloride, strontium chloride, barium chloride, lithium bromide, sodium bromide, potassium bromide, rubidium bromide, cesium bromide, berylium bromide, magnesium bromide, calcium bromide, strontium bromide, barium bromide, lithium iodide, sodium iodide, potassium iodide, rubidium iodide, cesium iodide, berylium iodide, magnesium iodide, calcium iodide, strontium iodide, barium iodide, lithium sulfate, sodium sulfate, potassium sulfate, rubidium sulfate, cesium sulfate, berylium sulfate, magnesium sulfate, calcium sulfate, strontium sulfate, barium sulfate, lithium borate, sodium borate, potassium borate, rubidium borate, cesium borate, berylium borate, magnesium borate, calcium borate, strontium borate, barium borate, lithium acetate, sodium acetate, potassium acetate, rubidium acetate, cesium acetate, berylium acetate, magnesium acetate, calcium acetate, strontium acetate, barium acetate, lithium carbonate, sodium carbonate, potassium carbonate, rubidium carbonate, cesium carbonate, berylium carbonate, magnesium carbonate, calcium carbonate, strontium carbonate, barium carbonate, lithium phosphate, sodium phosphate, potassium phosphate, rubidium phosphate, cesium phosphate, berylium phosphate, magnesium phosphate, calcium phosphate, strontium phosphate, and barium phosphate and preferably lithium fluoride, sodium fluoride, potassium fluoride, rubidium fluoride, cesium fluoride, berylium fluoride, magnesium fluoride, calcium fluoride, strontium fluoride, barium fluoride, lithium iodide, sodium iodide, potassium iodide, rubidium iodide, cesium iodide, berylium iodide, magnesium iodide, calcium iodide, strontium iodide, barium iodide, lithium sulfate, sodium sulfate, potassium sulfate, rubidium sulfate, cesium sulfate, berylium sulfate, magnesium sulfate, calcium sulfate, strontium sulfate, barium sulfate and more preferably lithium fluoride, sodium fluoride, potassium fluoride, rubidium fluoride, cesium fluoride, magnesium fluoride, calcium fluoride, strontium fluoride and barium fluoride, lithium sulfate, sodium sulfate, potassium sulfate, rubidium sulfate, cesium sulfate, magnesium sulfate, calcium sulfate, strontium sulfate, and barium sulfate.

Glyceryl carbonate and glycidol are suitable as intermediates for the preparation of polymers, e.g. epoxy resins, from glycidyl esters of polycarboxylic acids (*Helv. Chim Acta*, 60, 1845 (1977)) or glycidyl methacrylate as polymer crosslinkers (*Helv. Chirm. Acta.* 60, 1845 (1977))

EXAMPLES

EXAMPLE 1

Oxidative Carbonylation of Glycerol 138 g (1.5 mol) of glycerol and 14.9 g of copper(I) chloride were placed in a stirred glass autoclave having a capacity of 250 mL and heated to 110° C. On reaching the reaction temperature, under an overall pressure of 6 bar, a mixture of 80% of CO and 20% of $O_2$ was passed through (100 mL/min under standard pressure conditions). After a period of 63 h, the reaction was interrupted and the effluent subjected to GC analysis. The conversion was 47%, and glyceryl carbonate was the only detectable product.

EXAMPLE 2

Oxidative Carbonylation of Glycerol in an Inert Solvent 230 g (0.25 mol) of glycerol, 150 g of nitrobenzene and 2.5 g (0.025 mol) of copper(I) chloride in inert solvents were placed in a stirred glass autoclave having a capacity of 250 mL and heated to 130° C. On reaching the reaction temperature, under an overall pressure of 8 bar, a mixture of 95% of CO and 5% of $O_2$ was passed through (100 mL/min under standard pressure conditions). After a period of 20 h, the reaction was interrupted and the effluent subjected to GC analysis. The conversion was 96%, and glyceryl carbonate was the only detectable product. Comparable results would be possible using butyrolactone, tetramethyl urea, N,N-dimethylimidazol-2-one, or propylene carbonate as solvent.

EXAMPLE 3

Preparation of Glycidol 15 g of glyceryl carbonate and 1.5 g of catalyst were placed in a small-size distillation unit and evacuated to from 10 to 40 mbar. The mixture was encompassed by an oil bath having a temperature of 200° C. The volatile reaction products were subjected to GC analysis. The selectivities toward glycidol achieved are summarized in Table 1 below. Hydroxy-2-propanone was found as by-product.

TABLE

| | Percentage Selectivities | | | | | | | | |
|---|---|---|---|---|---|---|---|---|---|
| | F | Cl | Br | I | $H_2PO_4$ | $HPO_4$ | $PO_4$ | $SO_4$ | $B_4O_7$ |
| Li | 93 | 54 | 48 | 30 | | | | | |
| Na | 99 | 89 | 90 | 52 | 99 | 98 | 95 | 99 | 70 |
| K | 87 | 87 | 90 | 64 | 91 | | | | |
| Rb | 81 | 86 | 83 | 73 | | | | | |
| Cs | 82 | 82 | 84 | 84 | | | | | |
| Mg | | 16 | | | | | | | |
| Ca | 98 | 30 | | | | | | | |
| Ba | 50 | | | | | | | | |

EXAMPLE 4

Continuous Preparation of Glycidol 2 g of sodium sulfate were placed in a vertical, heated glass tube (diameter 2 cm, height 20 cm) and the apparatus was heated to 230° C. and evacuated to ca 100 mbar. Glyceryl carbonate was then metered in upwardly by means of an HPLC pump (0.5 mm/min). The gaseous products which escaped at the top of the reactor were isolated by condensation and subjected to GC analysis. The glyceryl carbonate conversion was 65%, whilst the selectivity toward glycidol was ca 92%. The by-products were almost exclusively non-volatile polymers, which remained in the reactor.

We claim:

1. A process for the preparation of glyceryl carbonate, which comprises reacting glycerol with carbon monoxide and oxygen in the presence of a copper catalyst at a temperature from 0°–180° C.

2. The process of claim 1, wherein the catalyst is a chloride, bromide, or trifluoroacetate of copper.

3. The process of claim 1, wherein the catalyst is copper chloride.

4. The process of claim 1, wherein the reaction is carried out at a temperature ranging from 80° to 150° C.

* * * * *